(12) United States Patent
Sarbou (10) Patent No.: US 11,832,045 B2
(45) Date of Patent: Nov. 28, 2023

(54) RING-SHAPED EARPHONE (71) Applicant: Kyle Richard Sarbou, Denver, CO (US)

(72) Inventor: Kyle Richard Sarbou, Denver, CO (US)

(*) Notice: Subject to any disclaimer, the term of this patent is extended or adjusted under 35 U.S.C. 154(b) by 65 days.

(21) Appl. No.: 17/831,410

(22) Filed: Jun. 2, 2022

(65) Prior Publication Data
US 2022/0394370 A1 Dec. 8, 2022

Related U.S. Application Data (60) Provisional application No. 63/196,094, filed on Jun. 2, 2021.

(51) Int. Cl.
H04R 1/10 (2006.01)
H04R 1/08 (2006.01)
G06F 3/16 (2006.01)
H04R 3/00 (2006.01)
A44C 9/00 (2006.01)
A61B 5/00 (2006.01)
H05K 7/14 (2006.01)
H04R 1/40 (2006.01)
H04N 23/57 (2023.01)
H04M 1/60 (2006.01)

(52) U.S. Cl.
CPC ......... *H04R 1/1016* (2013.01); *A44C 9/0053* (2013.01); *A61B 5/6817* (2013.01); *A61B 5/6826* (2013.01); *G06F 3/165* (2013.01); *H04N 23/57* (2023.01); *H04R 1/08* (2013.01); *H04R 1/1025* (2013.01); *H04R 1/1041* (2013.01); *H04R 1/1075* (2013.01); *H04R 1/406* (2013.01); *H04R 3/005* (2013.01); *H05K 7/1427* (2013.01); *H04M 1/6066* (2013.01); *H04R 2201/107* (2013.01); *H04R 2420/07* (2013.01)

(58) Field of Classification Search
CPC ....... A44C 9/0053; G06F 3/165; G06F 3/167; H04M 1/724095; H04R 1/08; H04R 1/1008; H04R 1/1016; H04R 1/1025; H04R 1/1075; H04R 1/1041; H04R 1/406; H04R 2420/07
See application file for complete search history.

(56) References Cited

U.S. PATENT DOCUMENTS

2020/0335856 A1* 10/2020 Kim .................. H01Q 1/273
2023/0276159 A1* 8/2023 Liu ..................... H04R 1/1091
381/370

* cited by examiner

*Primary Examiner* — Kile O Blair
(74) *Attorney, Agent, or Firm* — Leyendecker & Lemire LLC (57) ABSTRACT A ring-shaped earphone may be configured to be worn in an ear. When not worn in the ear, the ring-shaped earphone may be conveniently stored on a finger. In one example, the ring-shaped earphone may include a ring-shaped body defined by an outer cylindrical surface and an inner cylindrical surface. The earphone may include a speaker within the ring-shaped body. The speaker may be configured to project sound through a speaker opening in the outer cylindrical surface. The earphone may include a microphone within the housing. The microphone may be configured to receive sound through a microphone opening in the inner cylindrical surface.

20 Claims, 10 Drawing Sheets

RING-SHAPED EARPHONE

CROSS REFERENCE

This application claims the benefit of U.S. Provisional Patent Application No. 63/196,094, filed on Jun. 2, 2021, the disclosure of which is incorporated by reference in its entirety.

FIELD

This disclosure relates to earphones. More specifically, this disclosure relates to wireless ring-shaped earphones that can be worn in a human ear or stored around a finger or thumb.

BACKGROUND

Wireless earphones, also known as earbuds, are a popular audio accessory for mobile devices, such as smartphones and smart watches. Earphones may connect wirelessly to mobile devices via, for example, Bluetooth wireless technology. Earphones may include a speaker to produce sound. Earphones may include a microphone that allows the user to conduct a handsfree phone call.

When the earphones are removed from an individual's ears, the earphones can be stored in a pocket or case to protect them from loss or damage. In some situations, an individual may not have a pocket, case, or other clean, convenient place to store the earphones. For example, when an individual is jogging and approaches an intersection, the individual may remove their earphones so they can better hear and negotiate traffic. In another example, an individual at a store may choose to remove their earphones while checking out to allow the individual to interact with a cashier. In both situations, the individual may lack a convenient place to temporarily store the earphones when not in use.

BRIEF SUMMARY

An earphone is needed that can be conveniently stored on a person's body when not worn in an ear.

A ring-shaped earphone has been created. When not in use, the earphone can be worn as a ring on a finger. This functionality ensures that an individual always has a convenient place to store the earphone. Also, by being wearable on a finger, the earphone is more readily accessible than a typical earphone and is more likely to be readily available for use throughout the day, compared to traditional earphones that a person may only carry periodically during the day (e.g., while commuting or exercising). When an individual receives an unexpected phone call, they can easily remove the earphone from their finger and position it in their ear before accepting the call.

In one example, the earphone may be a flexible silicone ring that allows the earphone to be worn on a finger and then removed from the finger and contorted to fit within a concha of an ear. In another example, the earphone may be a flexible silicone ring that allows the earphone to be worn on a finger and then removed from the finger and contorted to fit partially within an ear canal and partially within a concha of an ear. The earphone may be constructed with electronic components that are interconnected by flexible electrical connections that permit flexing of the earphone to permit contorting a body of the earphone without damaging the electronic components or electrical connections within the earphone. The earphone may be water-resistant or waterproof.

The foregoing, together with other features and embodiments will become more apparent upon referring to the following specification, claims, and accompanying drawings. Embodiments of the invention covered by this application are defined by the claims below, not by this summary. This summary is a high-level overview of various aspects of the subject matter and introduces some of the concepts that are further described in the Detailed Description section below. This summary is not intended to identify key or essential features of the claimed subject matter, nor is it intended to be used in isolation to determine the scope of the claimed subject matter.

DETAILED DESCRIPTION

Figure 1:
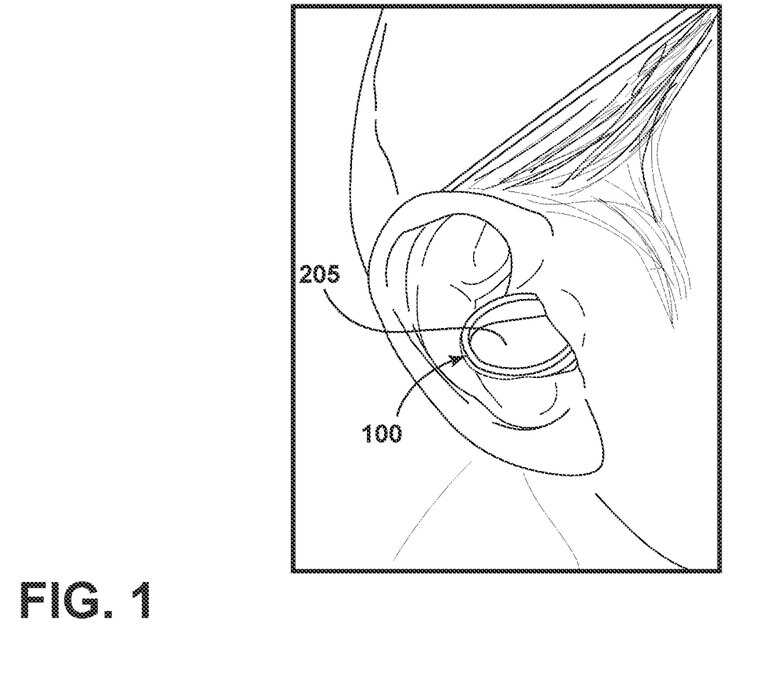
FIG. 1 shows a ring-shaped earphone positioned within a concha of an ear.
Figure 2:
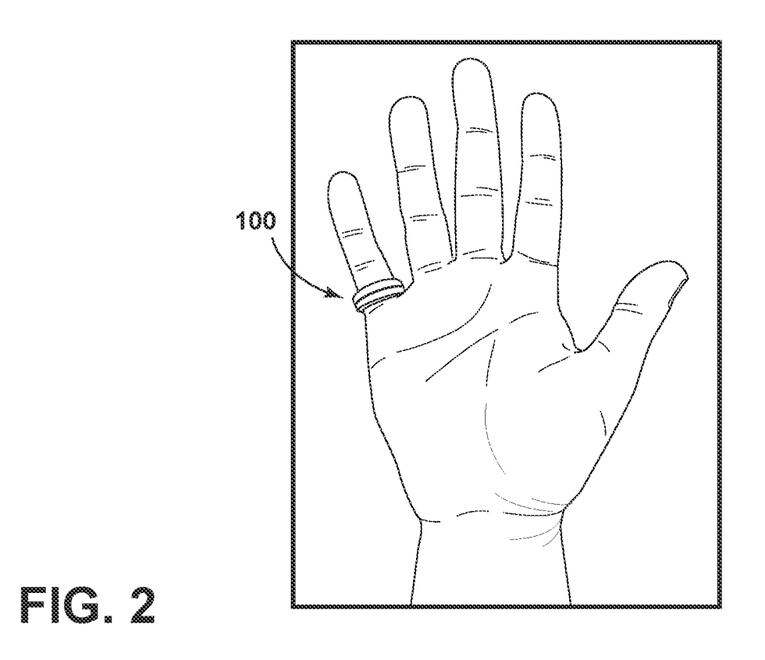
FIG. 2 shows the ring-shaped earphone of FIG. 1 worn on a finger.
Figure 5:
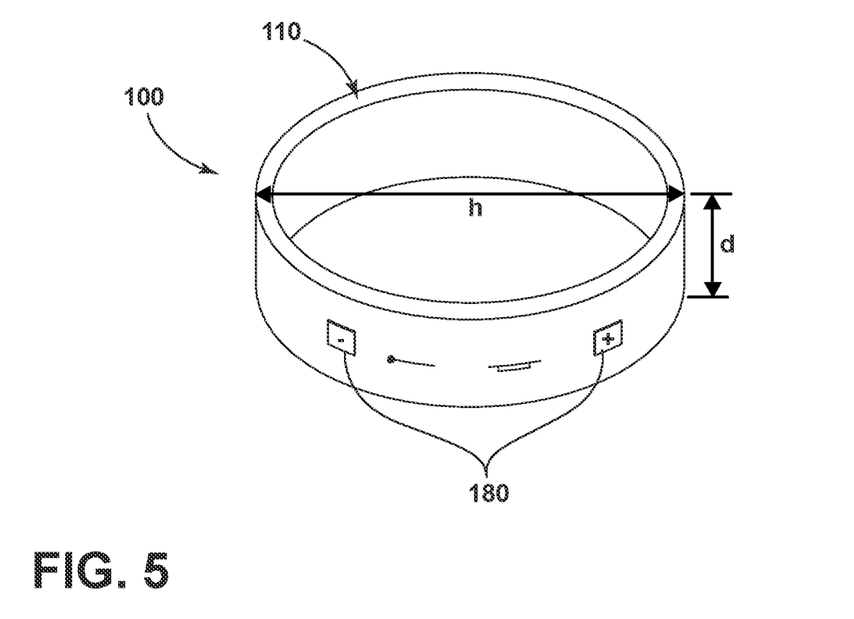
FIG. 5 shows control buttons located on the ring-shaped earphone of FIG. 1.
Figure 6:
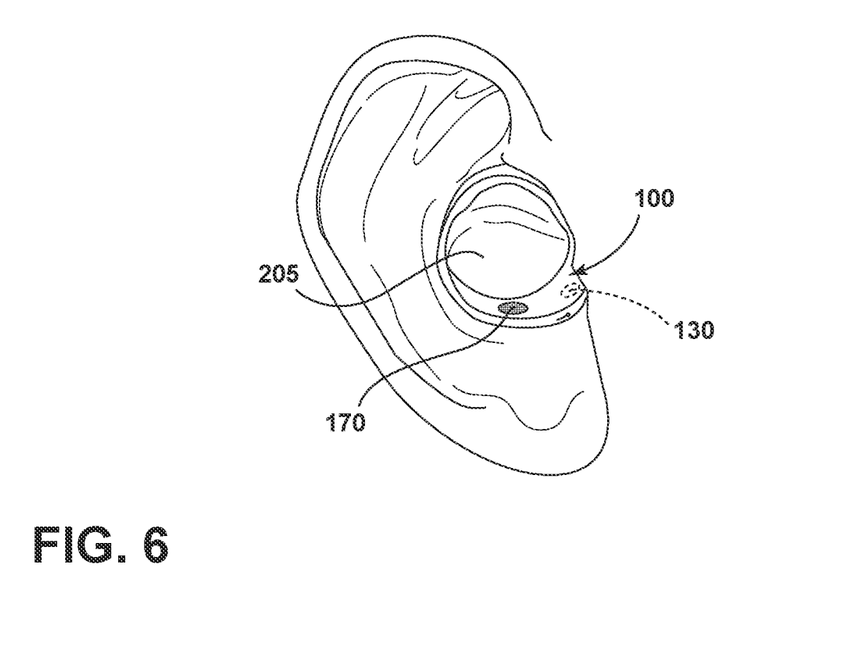
FIG. 6 shows the ring-shaped earphone of FIG. 1 positioned within a concha of an ear with a speaker on an outer cylindrical surface of the earphone and directed toward an ear canal and a microphone on an inner cylindrical surface of the earphone.
Figure 14:
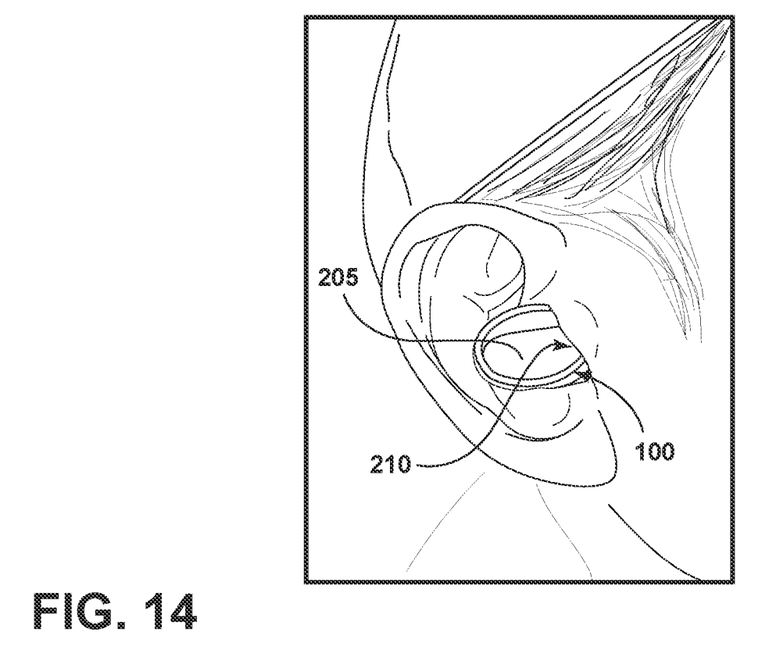
FIG. 14 shows a ring-shaped earphone worn partially in an ear canal and partially in a concha of the ear.
Figure 15:
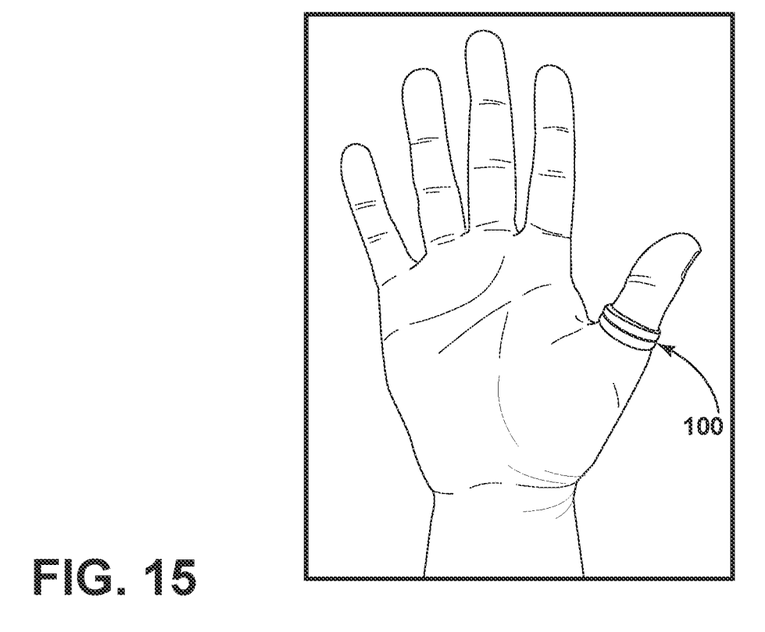
FIG. 15 shows the ring-shaped earphone of FIG. 14 worn on a thumb.

FIGS. 1-19 show various embodiments of ring-shaped earphones. When operating as an earphone, the ring-shaped earphone 100 can be worn in an ear, as shown in FIGS. 1, 6, and 14. When not operating as an earphone, the ring-shaped earphone 100 can be worn (i.e., stored) on a digit (e.g., finger or thumb) of a hand for safe keeping and easy access. FIG. 2 shows the ring-shaped earphone 100 worn on a finger. FIG. 15 shows the ring-shaped earphone 100 worn on a thumb.

Figure 4:
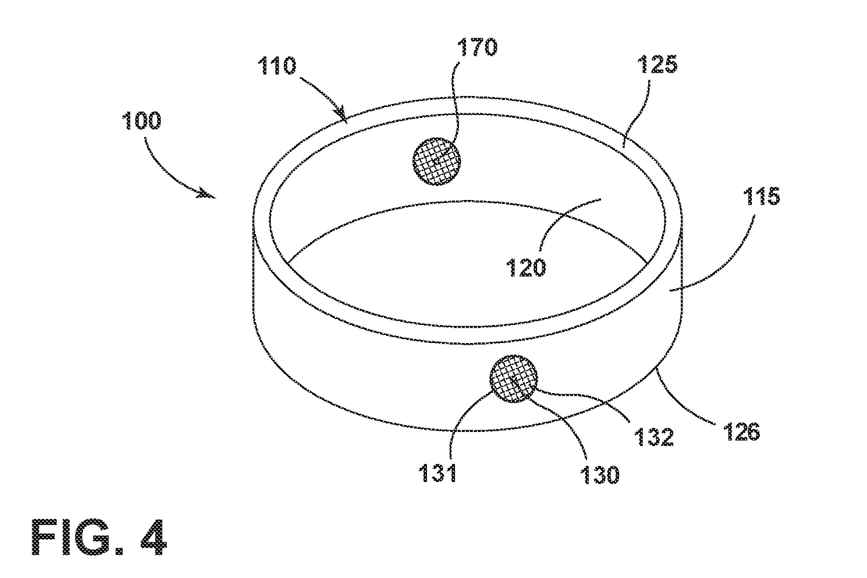
FIG. 4 shows a speaker located on an outer cylindrical surface of the ring-shaped earphone of FIG. 1 and a microphone located on an inner cylindrical surface of the ring-shaped earphone.

The ring-shaped earphone 100 may include a ring-shaped body 110, as shown in FIG. 4. The ring-shaped body 110 may serve as a ring-shaped housing for various components. The ring-shaped body 110 may include an outer surface that may be an outer cylindrical surface 115. The ring-shaped body 110 may include an inner surface that may be an inner cylindrical surface 120. The ring-shaped body 110 may include a first perimeter surface 125 extending from the outer cylindrical surface 115 to the inner cylindrical surface 120. The ring-shaped body 110 may include a second perimeter surface 126 extending from the outer cylindrical surface 115 to the inner cylindrical surface 120. The inner cylindrical surface 120 may define a through-hole configured to receive a digit of a hand and thereby allow the ring-shaped earphone 100 to be stored on the digit. When oriented upright in the ear, the ring-shaped body 110 may have a height (h) that is greater than a depth (d), as shown in FIG. 5. The height (h) may be more than twice the depth (d). The ring-shaped body 110 may be waterproof or water-resistant to protect electrical components from moisture-related damage resulting from, for example, precipitation or perspiration.

The ring-shaped body 110 may be constructed from a flexible material, such as an elastomer. One suitable example of an elastomer is silicone rubber. When force is applied to the outer surface, the ring-shaped body 110 may be configured to contort from a round shape to an eccentric shape or a nonsymmetric shape to permit insertion into the ear. In one example, the ring-shaped body 110 may be configured to fit within a concha 205 on the ear, as shown in FIG. 1. In another example, the ring-shaped body 110 may be configured to fit at least partially within an ear canal 210 and at least partially within the concha 205, as shown in FIG. 14. The concha 205 may be a depressed area at an opening of a middle ear. The concha 205 may be bounded, for example, by a tragus, an incisura, an antitragus, an antihelix, inferior crus of the antihelix, and a root of the helix. The concha 205 may be bisected by a cruss helix and may include a cymba above the cruss helix and a cavum below the cruss helix. The concha 205 may serve to direct sound into the ear canal 210.

Figure 3:
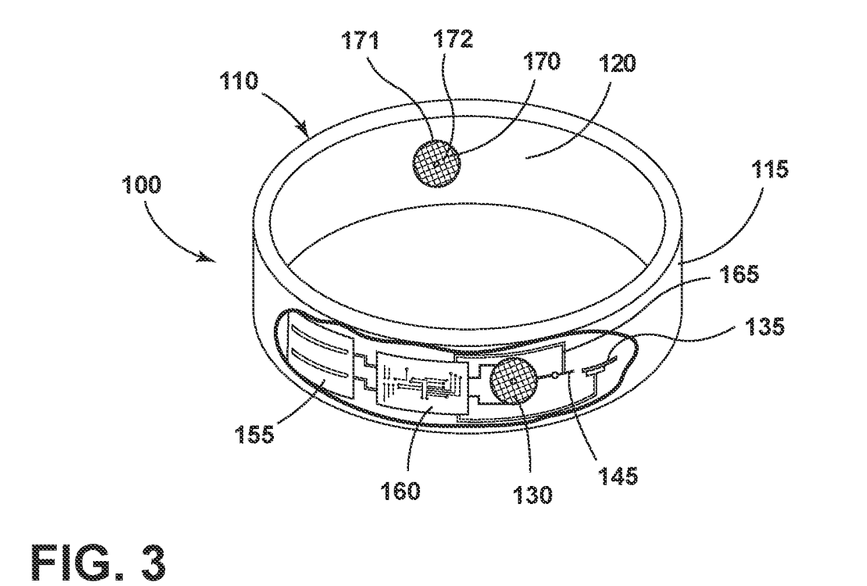
FIG. 3 shows a partial cutaway view of the ring-shaped earphone of FIG. 1 exposing electronic components within a ring-shaped body.

The ring-shaped body 110 may house a plurality of electronic components of the earphone 100, as shown in FIG. 3. The plurality of electronic components may enable the earphone 100 to receive an audio signal wirelessly and produce sound based on the received audio signal. The electronic components may be potted in a waterproof potting compound, such as an epoxy potting compound, and located in the ring-shaped body 110. The ring-shaped body 110 may include an electronic circuitry configured to receive and transmit audio information. The earphone 100 may include a circuit board 160. The circuit board 160 may be a flexible circuit board to permit contortion of the ring-shaped housing 110. The circuit board 160 may be a flexible circuit board including, for example, polyimides or transparent polyester. The earphone 100 may include a wireless receiver 135, such as a Bluetooth wireless receiver, configured to receive a signal from a mobile device. The earphone 100 may include a wireless transmitter 145, such as a Bluetooth wireless transmitter, configured to transmit a signal to a mobile device.

The ring-shaped body 110 may include a speaker 130. The speaker 130 may be any suitable type of speaker, such as, for example, a horn, electrodynamic speaker, flat panel speaker, or piezoelectric speaker. The speaker 130 may be a waterproof speaker. The speaker 130 may be located on at or proximate to the outer cylindrical surface 115 of the ring-shaped body 110, as shown in FIG. 4. The speaker 130 may be configured to project sound through a speaker opening 131 in the outer cylindrical surface of the ring-shaped body, as shown in FIG. 4. The speaker opening 131 may be covered with a waterproof or water-resistant membrane 132 that allows sound to exit but prevents water from entering the housing. In one example, the waterproof or water-resistant membrane 132 may be made of a polytetrafluoroethylene (PTFE) material, such as GORE-TEX. When the ring-shaped earphone 100 is positioned in the ear, the speaker 130 may be configured to project sound toward or into the individual's ear canal 210 leading to an eardrum. FIG. 6 shows a dashed circle depicting a location of the speaker 130 on the outer cylindrical surface 115 of the ring-shaped earphone 100. In another example, the speaker 130 may be located on at or proximate to the first or second perimeter surface 125, 126 of the ring-shaped body 110.

The ring-shaped body 110 may include electrical wiring 165, as shown in FIG. 3. The wiring 165 may electrically connect the various electronic components of the ring-shaped earphone 100. In embodiments where the ring-shaped body 110 is configured to be flexible to permit contortion, the wiring 165 may be thin and flexible wiring. In one example, the wiring 165 may be a metal foil.

The ring-shaped body 110 may include a microphone 170. The microphone 170 may be a waterproof microphone. In one example, the microphone 170 may be located on an inner cylindrical surface 120 of the ring-shaped body 110, as shown in FIG. 4. The microphone 170 may be configured to receive sound through a microphone opening 171 on the inner cylindrical surface 120 of the ring-shaped body 110. The microphone opening 171 may be covered with a waterproof or water-resistant membrane 172 that allows sound to enter but prevents water from entering the housing. Locating the microphone 170 on the inner cylindrical surface 120 may allow the microphone to effectively receive sound when the ring-shaped earphone 100 is installed in the ear and the outer cylindrical surface 115 is pressed against flesh of the ear. When the ring-shaped earphone 100 is worn on the finger, as shown in FIG. 2, the microphone may be covered by flesh of the finger and rendered ineffective, which may be desirable to prevent the microphone from capturing unwanted sound (e.g., when an unintended call is placed from the mobile device).

Figure 16:
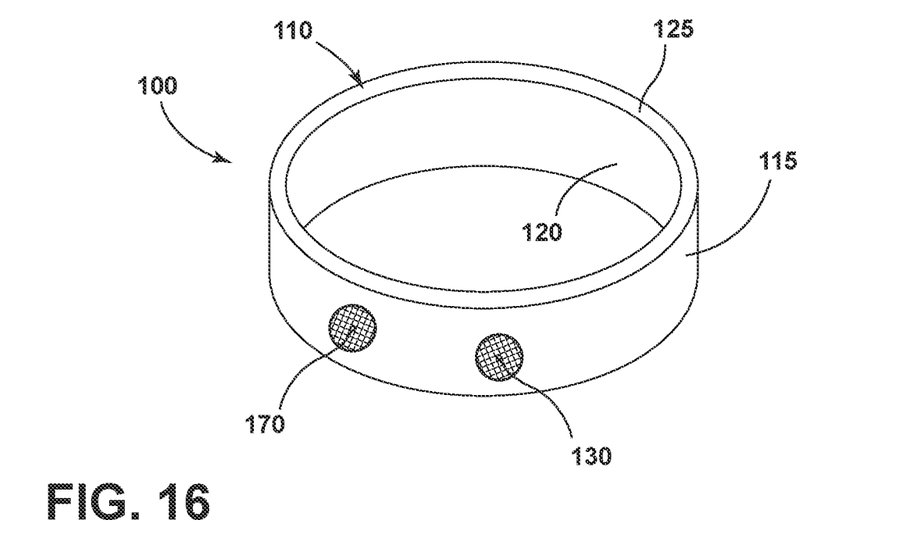
FIG. 16 shows an embodiment of a ring-shaped earphone with a speaker and microphone located on an outer cylindrical surface of a ring-shaped body.

In another example, the microphone 170 may be located on the perimeter surface 125 between the inner cylindrical surface 120 and the outer cylindrical surface 115. In yet another embodiment, the ring-shaped body 110 may include a microphone 170 and a speaker 130 on the outer cylindrical surface 115, as shown in FIG. 16. This configuration may allow an individual to handle a phone call while the ring remains on the individual's finger.

Figure 17:
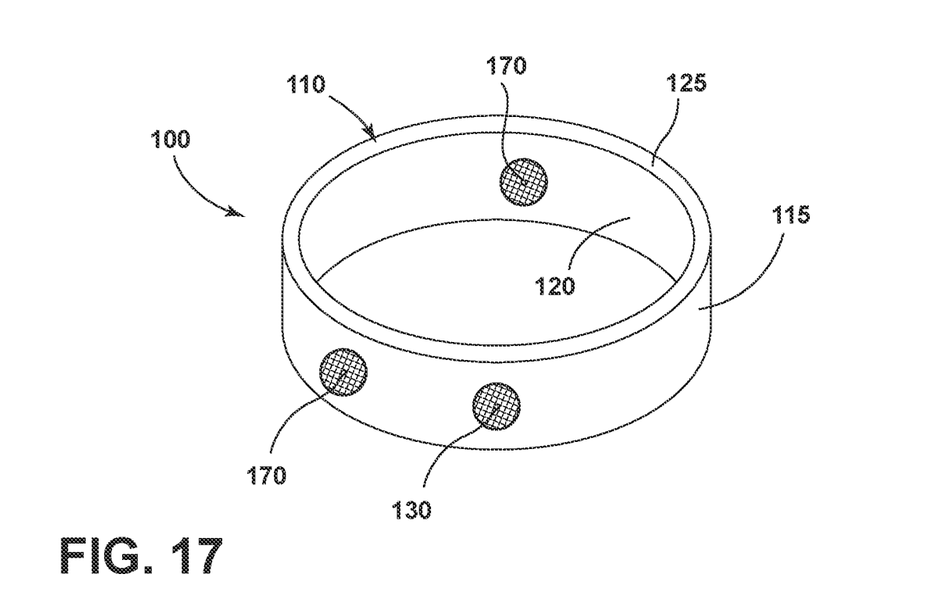
FIG. 17 shows an embodiment of a ring-shaped earphone with a speaker and first microphone located on an outer cylindrical surface of a ring-shaped body and a second microphone located on an inner cylindrical surface of the ring-shaped body.

In still another embodiment, the ring-shaped body 110 may include a first microphone 170 and a speaker 130 located on the outer cylindrical surface 115, as shown in FIG. 17. This configuration allows an individual to handle a phone call while the ring remains on the individual's finger. The ring-shaped body 110 may include a second microphone 170 on the inner cylindrical surface 120, which allows an individual to handle a phone call when the ring is worn in the ear. When the ring-shaped body 110 is installed in the ear, the first microphone 170 may be deactivated by a controller programmed to carry out the operation, and the second microphone 170 may be activated by the controller programmed to carry out the operation. When the ring-shaped body 110 is installed on the digit, the first microphone may be activated by the programmed controller, and the second microphone may be deactivated by the programmed controller. To determine position information (e.g., whether the ring-shaped body 110 is positioned in the ear, on the digit, or neither), and to determine which microphone to activate and which microphone to deactivate based on the position information, the device may include a skin detection device. The skin detection device may include one or more skin detection sensors 185. The skin detection sensors may include one or more infrared sensors configured to detect the presence of skin proximate to the inner cylindrical surface 120 and/or the outer cylindrical surface 115. In one example, the one or more infrared sensors may be short-wave infrared sensors. The short-wave infrared sensors may operate with a wavelength of about 1050 to 2500 nanometers.

The ring-shaped body 110 may house a battery 155, as shown in FIG. 3. The battery 155 may be a rechargeable battery. The battery 155 may be a rechargeable lithium-ion battery. The battery 155 may be a flexible (i.e., non-rigid) battery. The battery 155 may be a flexible, rechargeable battery. In one embodiment, the battery may be removable from the ring-shaped body 110. In another embodiment, the battery 155 may be permanently installed within the ring-shaped body 110.

Figure 11:
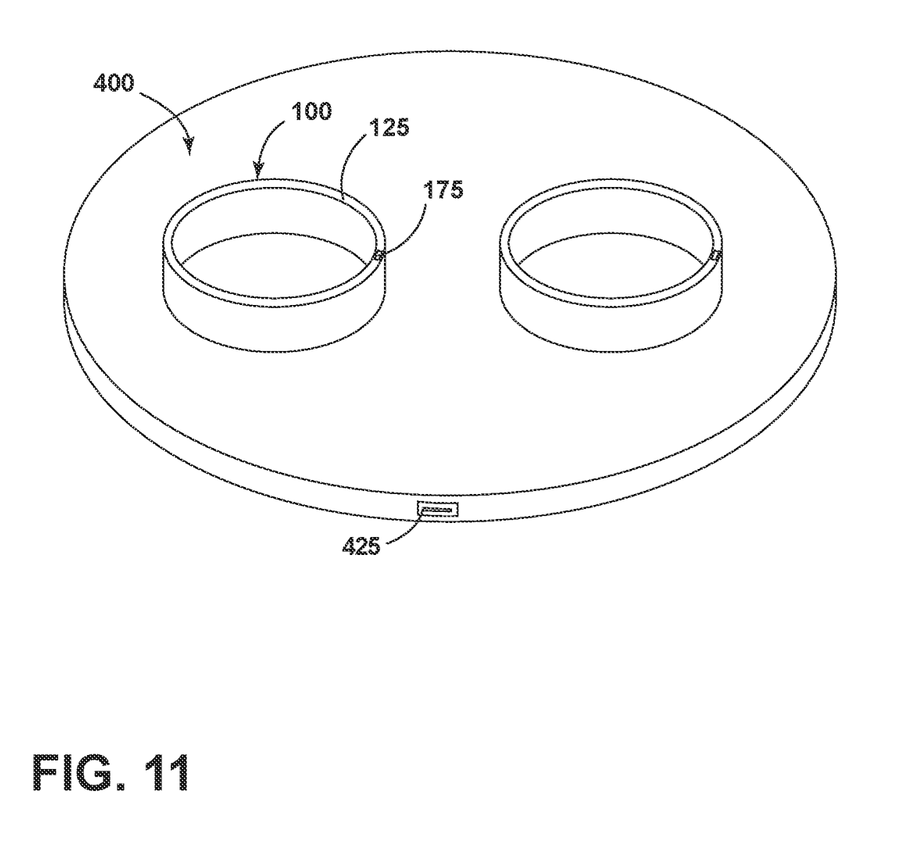
FIG. 11 shows a pair of ring-shaped earphones wirelessly charging on an inductive charging device.

The battery 155 may be charged by a charging device. The charging device may be incorporated within the ring-shaped body 110 or separate from the ring-shaped body. In one example, the charging device may include a charging port, such as a USB-type charging port. In another example, the charging device may include an inductive charging device, such as an inductive charging pad 400, as shown in FIG. 11. The charging pad 400 may include an electrical connection 425, such as a USB-type connection, that allows the charging pad 400 to connect to an electrical power source, such as an electrical outlet. The ring-shaped earphone may include a battery indicator light 175. When the earphones 100 are fully charged, the battery indicator light 175 on the earphone may change from a first color to a second color (e.g., from red to green). In another example, the charging device may include a kinetic charging device located within the ring-shaped body 110. In another example, the charging device may include a thermal charging device located within the ring-shaped body 110. In another example, the changing device may include a charging case, as shown in FIG. 7.

Figure 7:
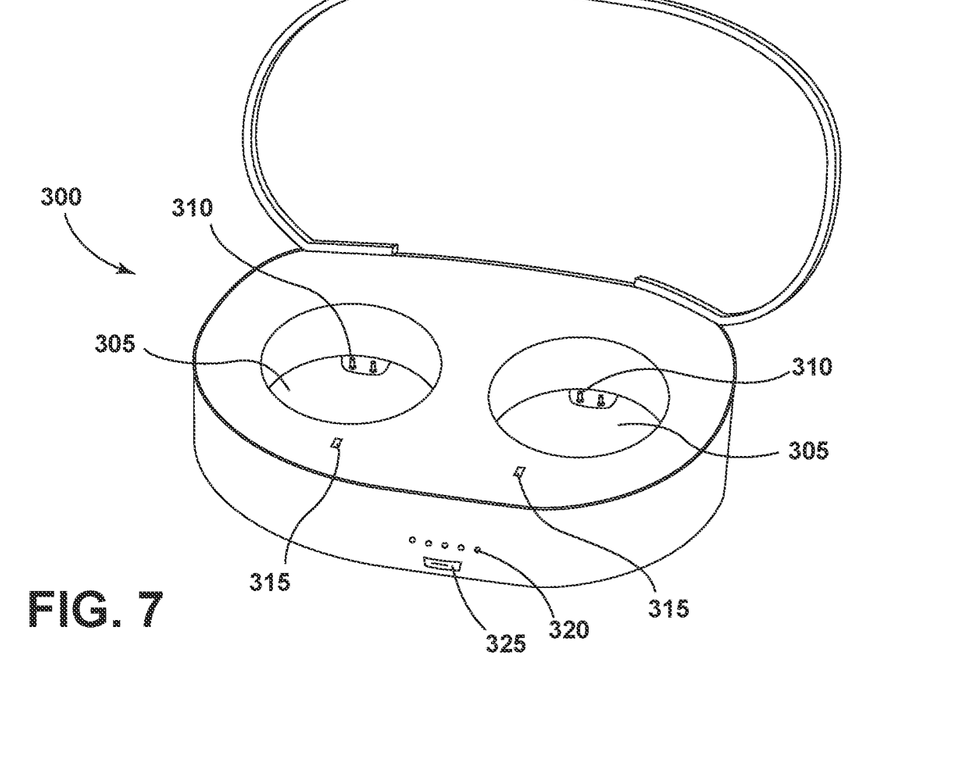
FIG. 7 shows a charging case for a pair of ring-shaped earphones.
Figure 8:
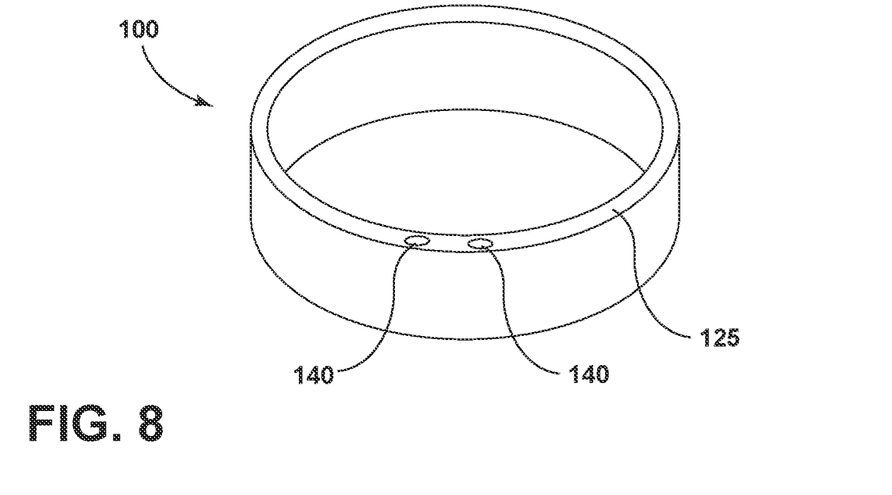
FIG. 8 shows a first embodiment of a ring-shaped earphone having electrical contacts for charging on a perimeter surface.
Figure 9:
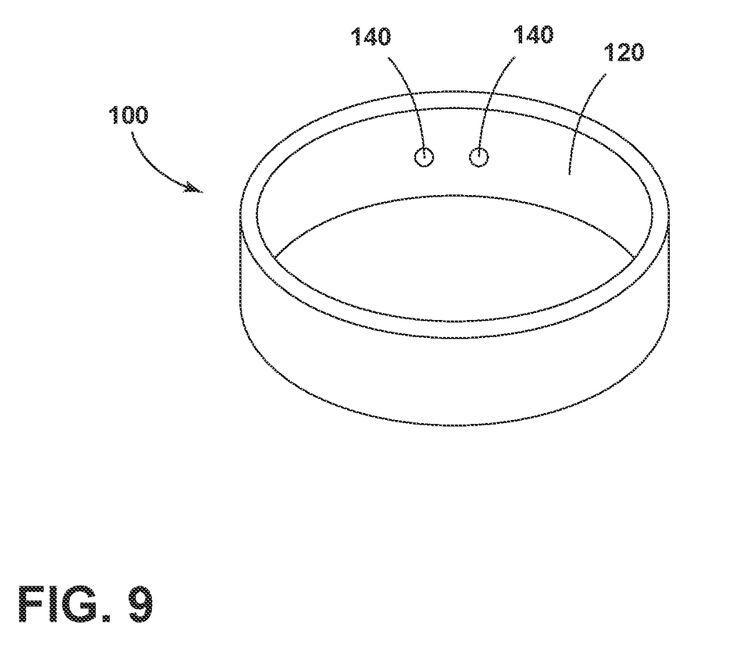
FIG. 9 shows a second embodiment of a ring-shaped earphone having electrical contacts for charging on the inner cylindrical surface.
Figure 10:
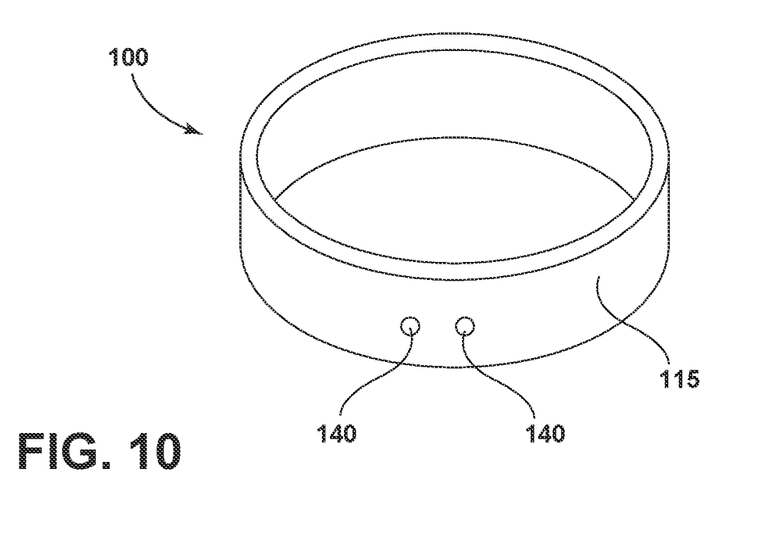
FIG. 10 shows a third embodiment of a ring-shaped earphone having electrical contacts for charging on the outer cylindrical surface.

The charging case 300 may be a clamshell case, as shown in FIG. 7. The charging case 300 may include a rechargeable battery. The charging case 300 may include an electrical connection 325, such as a USB-type connection, that allows the charging case to connect to an electrical power source, such as an electrical outlet. The charging case 300 may include a pair of cavities 305 configured to receive a pair of ring-shaped earphones. Each cavity 305 may include a pair of electrical contacts 310 configured to interface with electrical contacts 140 on the ring-shaped earphone 100 to facilitate charging of a battery 155 within each earphone. In the example shown in FIG. 8, the electrical contacts 140 may be located on the perimeter surface 125 of the ring-shaped earphone. In the example of FIG. 9, the electrical contacts 140 may be located on the inner cylindrical surface 120 of the ring-shaped earphone. In the example of FIG. 10, the electrical contacts 140 may be located on the outer cylindrical surface 115 of the ring-shaped earphone 100. Magnetic portions may aid in properly aligning the electrical contacts 310 of the charging case 300 with the electrical contacts 140 of the earphones 100. The charging case 300 may include one or more battery indicator lights 320. When the earphones 100 are fully charged, battery lights 315 on the charging case 300 may change from a first color to a second color. The number of indicator lights 320 that are illuminated may correspond to a battery charge level for the charging case 300. For example, if three of five lights are illuminated, the battery charge level may be approximately sixty percent of a full charge capacity.

The ring-shaped earphone 100 may include one or more controls 180. The ring-shaped earphone 100 may include one or more controls 180 on the ring-shaped body 110, as shown in FIG. 5. The controls 180 may include, for example, mechanical buttons or touch-activated buttons. The ring-shaped earphone 100 may include a power on/off button. The ring-shaped earphone 100 may include a play/pause button. The ring-shaped earphone 100 may include a song forward/back button. The ring-shaped earphone 100 may include a volume up/down button. The ring-shaped earphone 100 may include a call answer/end button. The ring-shaped earphone 100 may include a button for controlling a camera on a mobile device, such as a mobile phone, smart watch, smart glasses, or smart ring. The ring-shaped earphone 100 may include a button to initiate a mobile payment. The ring-shaped earphone 100 may include a button to activate a voice command mode on the ring-shaped earphone 100 or another mobile device. To reduce the number of buttons required without sacrificing functionality, any button may be configured to perform multiple functions. For example, touching or pressing a button once may pause and play audio, pressing the button twice may activate a voice command mode, and pressing the button for a longer duration may turn the ring-shaped earphone power on/off.

Figure 12:
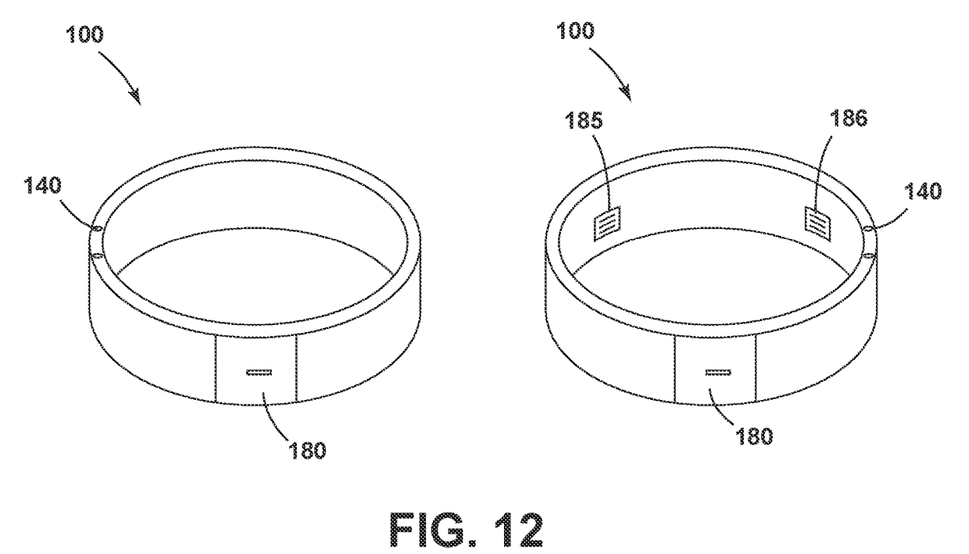
FIG. 12 shows a front perspective view of a pair of ring-shaped earphones.
Figure 13:
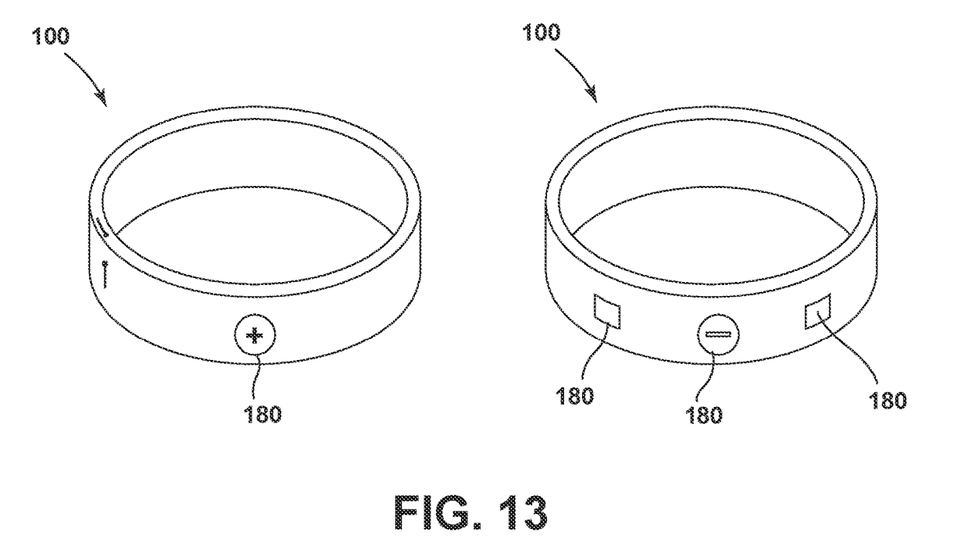
FIG. 13 shows a front perspective view of a pair of ring-shaped earphone.

The ring-shaped earphone 100 may include one or more sensors 185 or other devices 186 that expand functionality of the earphone beyond receiving and transmitting audio signals. For example, the ring-shaped earphone 100 may include a heart rate sensor 185, as shown in FIG. 12. The ring-shaped earphone 100 may include a temperature sensor. The ring-shaped earphone 100 may include a blood pressure sensor. The ring-shaped earphone 100 may include a blood oxygen sensor. The ring-shaped earphone 100 may include a pulse oximeter. The ring-shaped earphone 100 may include a pedometer. The ring-shaped earphone 100 may include a camera. The camera may include a lens that is located at the outer cylindrical surface 115. The ring-shaped earphone 100 may include a blood glucose monitoring device. The device 186 may be a light on the exterior surface 115 of the housing 110. The light may serve as a camera flash. The light may serve as a flashlight.

Figure 18:
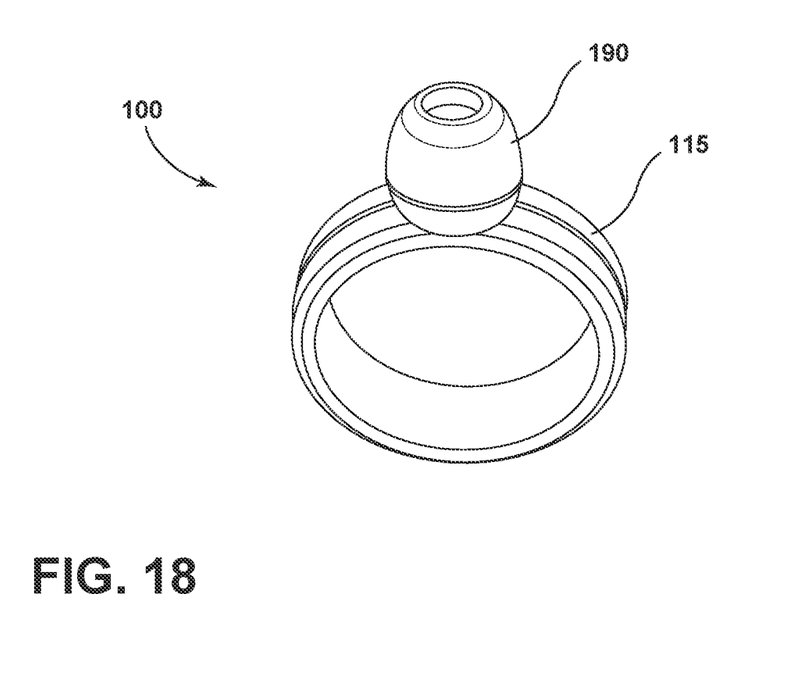
FIG. 18 shows a top perspective view of an embodiment of a ring-shaped earphone with an earbud protruding outwardly from the outer cylindrical surface of the ring-shaped body.
Figure 19:
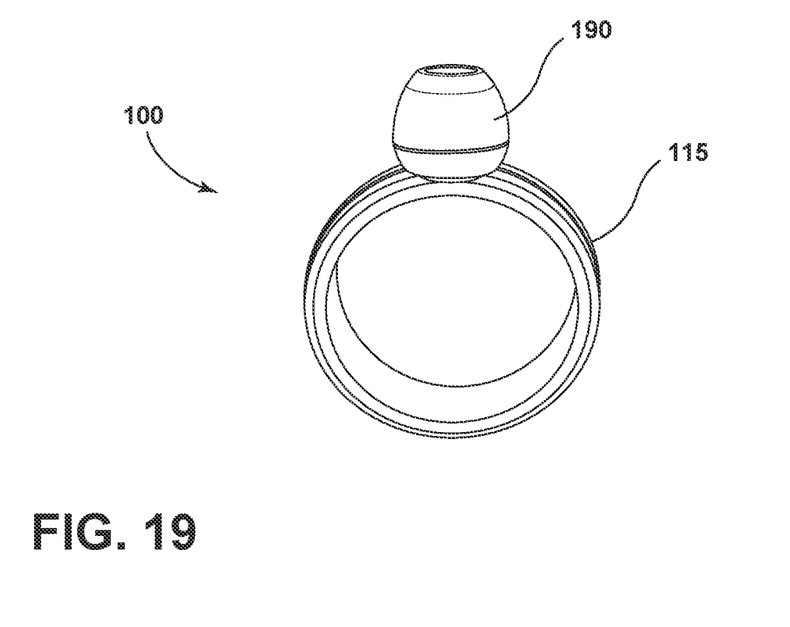
FIG. 19 shows a side perspective view of the ring-shaped earphone of FIG. 18.

In another example, shown in FIGS. 18 and 19, the ring-shaped earphone 100 may include an earbud 190 protruding from the outer surface 115 of the ring-shaped body 110. The earbud 190 may be permanently attached to the outer surface 115. The earbud 190 may be removably attached to the outer surface 115. The earbud 190 may be extendable and retractable from the ring body 110 through, for instance, inflation and deflation, respectively.

The ring-shaped earphone 100 can be manufactured in a variety of sizes to accommodate a variety of ear shapes and sizes and digit sizes. The ring-shaped earphone can be manufactured in a variety of colors.

The methods and compositions of the present invention can comprise, consist of, or consist essentially of the essential elements and limitations described herein, as well as any additional or optional steps, components, or limitations described herein or otherwise useful in the art.

It is understood that the invention is not confined to the particular construction and arrangement of parts herein illustrated and described, but embraces such modified forms thereof as come within the scope of the claims.

The foregoing description has been presented for purposes of illustration and description. It is not intended to be exhaustive or to limit the claims to the embodiments disclosed. Other modifications and variations may be possible in view of the above teachings. The embodiments were chosen and described to explain the principles of the invention and its practical application to enable others skilled in the art to best utilize the invention in various embodiments and various modifications as are suited to the particular use contemplated. It is intended that the claims be construed to include other alternative embodiments of the invention except insofar as limited by the prior art.

What is claimed is:

1. A ring-shaped earphone comprising:
a flexible ring-shaped housing comprising an outer cylindrical surface and an inner cylindrical surface;
a circuit board located in the flexible ring-shaped housing;
a rechargeable battery located in the flexible ring-shaped housing, the rechargeable battery being electrically connected to the circuit board;
a speaker within the flexible ring-shaped housing, the speaker being electrically connected to the circuit board and being electrically connected to the rechargeable battery, the speaker located at or proximate to the outer cylindrical surface of the flexible ring-shaped housing;
a microphone located in the flexible ring-shaped housing, the microphone being electrically connected to the circuit board and electrically connected to the rechargeable battery, the microphone located at or proximate to the inner cylindrical surface of the flexible ring-shaped housing; and
one or more control buttons on the outer cylindrical surface of the flexible ring-shaped housing,
wherein the inner cylindrical surface defines a through-hole configured to receive a digit of a hand, the through-hole allowing the ring-shaped earphone to be stored on the digit, and
wherein the ring-shaped earphone is configured to be contorted into a nonsymmetrical shape and worn in a concha of an ear with the speaker oriented to project sound into an ear canal.

2. The ring-shaped earphone of claim 1, further comprising a sensor that is electrically connected to the circuit board and electrically connected to the rechargeable battery, wherein the sensor is selected from a group of sensors consisting of a heart rate sensor, a temperature sensor, a pedometer, and a pulse oximeter.

3. The ring-shaped earphone of claim 1, further comprising a camera that is electrically connected to the circuit board and electrically connected to the rechargeable battery, the camera having a lens that is located at the outer cylindrical surface.

4. The ring-shaped earphone of claim 1, further comprising a charging device, wherein the charging device is selected from a group consisting of an inductive charging device, a kinetic charging device, and a thermal charging device.

5. The ring-shaped earphone of claim 1, wherein the rechargeable battery is a flexible rechargeable battery.

6. The ring-shaped earphone of claim 1, wherein the circuit board is a flexible circuit board.

7. The ring-shaped earphone of claim 6, wherein the flexible circuit board comprises an electrical connection comprising metal foil.

8. A ring-shaped earphone comprising:
a flexible ring-shaped body comprising an outer surface and an inner surface;
a speaker in the flexible ring-shaped body, the speaker located at or proximate to the outer surface; and
a microphone in the flexible ring-shaped body, the microphone located at or proximate to the inner surface,
wherein the ring-shaped earphone is configured to be contorted and worn at least partially within a concha of an ear to project sound from the speaker toward an eardrum when in use, and
wherein the ring-shaped earphone is configured to be stored on a digit of a hand when not in use.

9. The ring-shaped earphone of claim 8, wherein the microphone is located at or proximate to an opening in the inner surface.

10. The ring-shaped earphone of claim 9, further comprising a waterproof or water-resistant membrane covering the opening in the inner surface.

11. The ring-shaped earphone of claim 8, wherein the speaker is located at or proximate to an opening in the outer surface.

12. The ring-shaped earphone of claim 11, further comprising a waterproof or water-resistant membrane covering the opening in the outer surface.

13. The ring-shaped earphone of claim 8, wherein the flexible ring-shaped body has a height and a depth, the height being greater than the depth.

14. The ring-shaped earphone of claim 8, further comprising a blood glucose monitoring device located within the flexible ring-shaped body.

15. A ring-shaped earphone comprising:
a ring-shaped housing defined at least in part by an outer cylindrical surface and an inner cylindrical surface;
a speaker within the ring-shaped housing, the speaker configured to project sound through a speaker opening in the outer cylindrical surface; and
a microphone within the ring-shaped housing, the microphone configured to receive sound through a microphone opening in the inner cylindrical surface,
wherein the ring-shaped earphone can be worn on a digit of a hand,
wherein the ring-shaped earphone can be worn at least partially within a concha and at least partially within an ear canal.

16. The ring-shaped earphone of claim 15, wherein the ring-shaped housing comprises a flexible silicone material.

17. The ring-shaped earphone of claim 15, further comprising:
a first waterproof or water-resistant membrane covering the speaker opening; and a second waterproof or water-resistant membrane covering the microphone opening.

18. The ring-shaped earphone of claim 15, further comprising a second microphone within the ring-shaped housing, the second microphone configured to receive sound through a second microphone opening in the outer cylindrical surface.

19. The ring-shaped earphone of claim 15, further comprising:
- a first skin detection sensor configured to detect a presence of skin proximate to the inner cylindrical surface; and
- a second skin detection sensor configured to detect a presence of skin proximate to the outer cylindrical surface.

20. The ring-shaped earphone of claim 15, further comprising:
- a first skin detection sensor configured to detect a presence of skin proximate to the inner cylindrical surface; and
- a second skin detection sensor configured to detect a presence of skin proximate to the outer cylindrical surface,
- wherein each of the first skin detection sensor and the second skin detection sensor is a short-wave infrared sensor configured to operate at a wavelength of about 1050 to 2500 nanometers.

* * * * *